US011266799B2

(12) United States Patent
Fuller et al.

(10) Patent No.: US 11,266,799 B2
(45) Date of Patent: Mar. 8, 2022

(54) IN-LINE NASAL DELIVERY DEVICE

(71) Applicant: Impel NeuroPharma, Inc., Seattle, WA (US)

(72) Inventors: Christopher Fuller, Seattle, WA (US); John D. Hoekman, Seattle, WA (US); Craig Kohring, Seattle, WA (US)

(73) Assignee: Impel Neuropharma, Inc., Seattle, WA (US)

(*) Notice: Subject to any disclaimer, the term of this patent is extended or adjusted under 35 U.S.C. 154(b) by 57 days.

(21) Appl. No.: 15/759,447

(22) PCT Filed: Sep. 9, 2016

(86) PCT No.: PCT/US2016/051169
§ 371 (c)(1),
(2) Date: Mar. 12, 2018

(87) PCT Pub. No.: WO2017/044897
PCT Pub. Date: Mar. 16, 2017

(65) Prior Publication Data
US 2018/0256836 A1 Sep. 13, 2018

Related U.S. Application Data

(60) Provisional application No. 62/216,789, filed on Sep. 10, 2015.

(51) Int. Cl.
*A61M 15/08* (2006.01)
*A61M 15/00* (2006.01)
*A61M 11/02* (2006.01)

(52) U.S. Cl.
CPC ............ *A61M 15/08* (2013.01); *A61M 11/02* (2013.01); *A61M 15/009* (2013.01); *A61M 2210/0618* (2013.01)

(58) Field of Classification Search
CPC .... A16M 15/08; A61M 11/02; A61M 15/009; A61M 2210/0618; A61M 15/0003;
(Continued)

(56) References Cited

U.S. PATENT DOCUMENTS 2,933,259 A 4/1960 Raskin
3,157,179 A 11/1964 Paullus et al.
(Continued)

FOREIGN PATENT DOCUMENTS

BE 1006872 A 1/1995
CN 201759968 U 3/2011
(Continued)

OTHER PUBLICATIONS

Alfonso R. Gennaro (Remington' s: the Science and Practice of Pharmacy, 1995, nineteenth Edition, vol. 1, p. 806) (Year: 1995).*
(Continued)

*Primary Examiner* — Kendra D Carter
*Assistant Examiner* — Arielle Wolff
(74) *Attorney, Agent, or Firm* — Fenwick & West LLP

(57) ABSTRACT

A delivery device for a compound including: a housing, vial holding a compound; and a source of propellant, wherein the housing provides an inlet and an outlet for the vial, wherein the inlet is in fluid communication with the source of propellant and is directed against the in-line nasal delivery device compound and the outlet allows for delivery of the compound.

12 Claims, 9 Drawing Sheets

(58) Field of Classification Search
CPC ...... A61M 16/12; A61M 11/00; A61M 15/00; A61M 11/06; A61M 11/08; A61M 15/08; A61P 11/00; A61P 11/02–11/16; B05B 11/06; B05B 7/04; B05B 7/12; G01F 11/02
See application file for complete search history.

(56) References Cited

U.S. PATENT DOCUMENTS

| | | | |
|---|---|---|---|
| 3,425,414 | A | 2/1969 | Roche |
| 3,704,812 | A * | 12/1972 | Marand .................. B65D 83/60 222/136 |
| 3,741,443 | A | 6/1973 | Marand |
| 3,888,253 | A | 6/1975 | Watt et al. |
| 3,906,950 | A | 9/1975 | Cocozza |
| 3,908,654 | A | 9/1975 | Lhoest et al. |
| 3,921,857 | A * | 11/1975 | Riccio ..................... G01F 11/32 222/145.5 |
| 3,971,377 | A | 7/1976 | Damani |
| 3,982,668 | A | 9/1976 | Riccio |
| 4,095,596 | A | 6/1978 | Grayson |
| 4,187,985 | A | 2/1980 | Goth |
| 4,227,522 | A | 10/1980 | Carris |
| 4,353,365 | A | 10/1982 | Hallworth et al. |
| 4,412,573 | A | 11/1983 | Zdeb |
| 4,462,983 | A | 7/1984 | Azria et al. |
| 4,620,670 | A | 11/1986 | Hughes |
| 4,702,415 | A | 10/1987 | Hughes |
| 4,896,832 | A | 1/1990 | Howlett |
| 4,995,385 | A | 2/1991 | Valentini et al. |
| 5,224,471 | A | 7/1993 | Marelli et al. |
| 5,307,953 | A | 5/1994 | Regan |
| 5,331,954 | A | 7/1994 | Rex et al. |
| 5,349,947 | A | 9/1994 | Newhouse et al. |
| 5,382,236 | A | 1/1995 | Otto et al. |
| 5,398,850 | A | 3/1995 | Sancoff et al. |
| 5,435,282 | A | 7/1995 | Haber et al. |
| 5,505,193 | A | 4/1996 | Ballini et al. |
| 5,516,006 | A | 5/1996 | Meshberg |
| 5,711,488 | A | 1/1998 | Lund |
| 5,715,811 | A | 2/1998 | Ohki et al. |
| 5,756,483 | A | 5/1998 | Merkus |
| 5,797,390 | A | 8/1998 | McSoley |
| 5,814,020 | A | 9/1998 | Gross |
| 5,819,730 | A | 10/1998 | Stone et al. |
| 5,823,183 | A | 10/1998 | Casper et al. |
| 5,881,719 | A | 3/1999 | Gottenauer et al. |
| 5,901,703 | A | 5/1999 | Ohki et al. |
| 5,906,198 | A | 5/1999 | Flickinger |
| 5,910,301 | A | 6/1999 | Farr et al. |
| 5,942,251 | A | 8/1999 | Merkus |
| 5,954,696 | A | 9/1999 | Ryan |
| 6,062,213 | A | 5/2000 | Fuisz et al. |
| 6,092,522 | A | 7/2000 | Calvert et al. |
| 6,145,703 | A | 11/2000 | Opperman |
| 6,158,676 | A | 12/2000 | Hughes |
| 6,180,603 | B1 | 1/2001 | Frey |
| 6,186,141 | B1 | 2/2001 | Pike et al. |
| 6,189,739 | B1 | 2/2001 | von Schuckmann |
| 6,294,153 | B1 | 9/2001 | Modi |
| 6,302,101 | B1 | 10/2001 | Py |
| 6,313,093 | B1 | 11/2001 | Frey |
| 6,347,789 | B1 | 2/2002 | Rock |
| 6,367,471 | B1 | 4/2002 | Genosar et al. |
| 6,367,473 | B1 | 4/2002 | Käfer |
| 6,382,465 | B1 | 5/2002 | Greiner Perth |
| 6,410,046 | B1 | 6/2002 | Lerner |
| 6,491,940 | B1 | 12/2002 | Levin |
| 6,540,983 | B1 | 4/2003 | Adjei et al. |
| 6,569,463 | B2 | 5/2003 | Patel et al. |
| 6,585,172 | B2 | 7/2003 | Arghyris |
| 6,585,957 | B1 | 7/2003 | Adjei et al. |
| 6,585,958 | B1 | 7/2003 | Keller et al. |
| 6,595,202 | B2 | 7/2003 | Gañán Calvo |
| 6,622,721 | B2 | 9/2003 | Vedrine et al. |
| 6,644,305 | B2 | 11/2003 | MacRae et al. |
| 6,644,309 | B2 | 11/2003 | Casper et al. |
| 6,647,980 | B1 | 11/2003 | Gizurarson |
| 6,681,767 | B1 | 1/2004 | Patton et al. |
| 6,684,879 | B1 | 2/2004 | Coffee et al. |
| 6,701,916 | B2 | 3/2004 | Mezzoli |
| 6,715,485 | B1 | 4/2004 | Djupesland |
| 6,734,162 | B2 | 5/2004 | Van Antwerp et al. |
| 6,810,872 | B1 | 11/2004 | Ohki et al. |
| 6,923,988 | B2 | 8/2005 | Patel et al. |
| 7,033,598 | B2 | 4/2006 | Lerner |
| 7,051,734 | B2 | 5/2006 | Casper et al. |
| 7,163,013 | B2 | 1/2007 | Harrison |
| 7,182,277 | B2 | 2/2007 | Vedrine et al. |
| 7,200,432 | B2 | 4/2007 | Lerner et al. |
| 7,214,209 | B2 | 5/2007 | Mazzoni |
| 7,231,919 | B2 | 6/2007 | Giroux |
| 7,258,119 | B2 | 8/2007 | Mazzoni |
| 7,296,566 | B2 | 11/2007 | Alchas |
| 7,347,201 | B2 | 3/2008 | Djupesland |
| 7,377,901 | B2 | 5/2008 | Djupesland et al. |
| 7,476,689 | B2 | 1/2009 | Santus et al. |
| 7,481,218 | B2 | 1/2009 | Djupesland |
| 7,543,581 | B2 | 6/2009 | Djupesland |
| 7,597,216 | B2 * | 10/2009 | Behar ................. B05B 11/3085 222/135 |
| 7,655,619 | B2 | 2/2010 | During et al. |
| 7,740,014 | B2 | 6/2010 | Djupesland |
| 7,784,460 | B2 | 8/2010 | Djupesland et al. |
| 7,799,337 | B2 | 9/2010 | Levin |
| 7,832,394 | B2 | 11/2010 | Schechter et al. |
| 7,841,337 | B2 | 11/2010 | Djupesland |
| 7,841,338 | B2 | 11/2010 | Dunne et al. |
| 7,854,227 | B2 | 12/2010 | Djupesland |
| 7,866,316 | B2 | 1/2011 | Giroux |
| 7,905,229 | B2 | 3/2011 | Giroux et al. |
| 7,934,503 | B2 | 5/2011 | Djupesland et al. |
| 7,975,690 | B2 | 7/2011 | Djupesland |
| 7,994,197 | B2 | 8/2011 | Cook et al. |
| 8,001,963 | B2 | 8/2011 | Giroux |
| 8,047,202 | B2 | 11/2011 | Djupesland |
| 8,119,639 | B2 | 2/2012 | Cook et al. |
| 8,122,881 | B2 | 2/2012 | Giroux |
| 8,146,589 | B2 | 4/2012 | Djupesland |
| 8,148,377 | B2 | 4/2012 | Cook et al. |
| 8,171,929 | B2 | 5/2012 | Djupesland et al. |
| 8,327,844 | B2 | 12/2012 | Djupesland |
| 8,408,427 | B2 | 4/2013 | Wong |
| 8,448,637 | B2 | 5/2013 | Giroux |
| 8,511,303 | B2 | 8/2013 | Djupesland |
| 8,517,026 | B2 | 8/2013 | Amon |
| 8,522,778 | B2 | 9/2013 | Djupesland |
| 8,550,073 | B2 | 10/2013 | Djupesland |
| 8,555,877 | B2 | 10/2013 | Djupesland |
| 8,555,878 | B2 | 10/2013 | Djupesland |
| 8,596,278 | B2 | 12/2013 | Djupesland |
| 8,733,342 | B2 | 5/2014 | Giroux et al. |
| 8,757,146 | B2 | 6/2014 | Hoekman et al. |
| 8,800,555 | B2 | 8/2014 | Djupesland |
| 8,839,790 | B2 | 9/2014 | Beck Arnon |
| 8,875,794 | B2 | 11/2014 | Carlsen et al. |
| 8,899,229 | B2 | 12/2014 | Djupesland et al. |
| 8,899,230 | B2 | 12/2014 | Immel |
| 8,910,629 | B2 | 12/2014 | Djupesland et al. |
| 8,925,544 | B2 | 1/2015 | Flickinger |
| 8,978,647 | B2 | 3/2015 | Djupesland et al. |
| 8,987,199 | B2 | 3/2015 | Abdel Maksoud et al. |
| 9,010,325 | B2 | 4/2015 | Djupesland |
| 9,038,630 | B2 | 5/2015 | Djupesland et al. |
| 9,067,034 | B2 | 6/2015 | Djupesland et al. |
| 9,072,857 | B2 | 7/2015 | Djupesland |
| 9,101,539 | B2 | 8/2015 | Nagata et al. |
| 9,119,932 | B2 | 9/2015 | Djupesland |
| 9,180,264 | B2 | 11/2015 | Young et al. |
| 9,272,104 | B2 | 3/2016 | Djupesland |
| 9,446,207 | B2 | 9/2016 | Jung |
| 9,550,036 | B2 * | 1/2017 | Hoekman ............ A61M 11/007 |
| 9,649,456 | B2 | 5/2017 | Djupesland et al. |
| 9,833,451 | B2 | 12/2017 | Cook et al. |

(56) References Cited

U.S. PATENT DOCUMENTS

| | | |
|---|---|---|
| 2002/0017294 A1 | 2/2002 | Py |
| 2002/0054856 A1 | 5/2002 | Jones |
| 2002/0092520 A1 | 7/2002 | Casper et al. |
| 2003/0017119 A1 | 1/2003 | Rabinowitz et al. |
| 2003/0091513 A1 | 5/2003 | Mohsen et al. |
| 2003/0114476 A1 | 6/2003 | Plachetka et al. |
| 2003/0158527 A1 | 8/2003 | Mezzoli |
| 2003/0198669 A1 | 10/2003 | Cutler et al. |
| 2003/0217748 A1 | 11/2003 | Giroux |
| 2004/0068222 A1 | 4/2004 | Brian |
| 2004/0238574 A1 | 12/2004 | Merk et al. |
| 2005/0023376 A1 | 2/2005 | Anderson |
| 2005/0028812 A1 | 2/2005 | Djupesland |
| 2005/0036985 A1 | 2/2005 | Ensoli |
| 2005/0098172 A1 | 5/2005 | Anderson |
| 2005/0142072 A1 | 6/2005 | Birch et al. |
| 2005/0274378 A1 | 12/2005 | Bonney et al. |
| 2006/0107957 A1 | 5/2006 | Djupesland |
| 2006/0147389 A1 | 7/2006 | Staniforth et al. |
| 2006/0219813 A1 | 10/2006 | Morrison |
| 2006/0240092 A1 | 10/2006 | Breitenkamp et al. |
| 2006/0246070 A1 | 11/2006 | Heavner et al. |
| 2007/0056585 A1 | 3/2007 | Davies et al. |
| 2007/0068514 A1 | 3/2007 | Giroux |
| 2007/0074722 A1 | 4/2007 | Giroux et al. |
| 2007/0119451 A1 | 5/2007 | Wang et al. |
| 2007/0131224 A1 | 6/2007 | Giroux |
| 2007/0172517 A1 | 7/2007 | Ben Sasson et al. |
| 2007/0202051 A1 | 8/2007 | Schuschnig |
| 2007/0253913 A1 | 11/2007 | Mohsen et al. |
| 2008/0017190 A1 | 1/2008 | Anandampillai et al. |
| 2008/0054099 A1 | 3/2008 | Giroux et al. |
| 2008/0163874 A1 | 7/2008 | Djupesland |
| 2008/0178871 A1 | 7/2008 | Genova et al. |
| 2008/0223363 A1 | 9/2008 | Djupesland |
| 2008/0305077 A1 | 12/2008 | Frey et al. |
| 2009/0216183 A1* | 8/2009 | Minotti ............ A61M 15/0003 604/82 |
| 2009/0320832 A1 | 12/2009 | Djupestand |
| 2010/0081663 A1 | 4/2010 | Cook et al. |
| 2010/0199984 A1 | 8/2010 | Williams, III et al. |
| 2010/0242958 A1 | 9/2010 | Jinks et al. |
| 2011/0045088 A1* | 2/2011 | Tsutsui ................. A61M 15/08 424/490 |
| 2011/0053859 A1 | 3/2011 | Deadwyler et al. |
| 2012/0195959 A1 | 8/2012 | Ishii |
| 2013/0180524 A1 | 7/2013 | Shahaf et al. |
| 2013/0327323 A1 | 12/2013 | Rubin |
| 2014/0014104 A1* | 1/2014 | Hoekman ............ A61M 15/08 128/203.12 |
| 2014/0034051 A1 | 2/2014 | Addington et al. |
| 2014/0083424 A1* | 3/2014 | Hoekman ................ B05B 7/08 128/203.22 |
| 2014/0170220 A1 | 6/2014 | Cartt et al. |
| 2014/0343494 A1 | 11/2014 | Hoekman et al. |
| 2015/0057287 A1 | 2/2015 | Cook et al. |
| 2015/0216823 A1 | 8/2015 | Chatterjee |
| 2015/0258178 A1 | 9/2015 | Gong |
| 2016/0101245 A1 | 4/2016 | Hoekman et al. |
| 2016/0228433 A1 | 8/2016 | Haruta et al. |
| 2016/0367771 A1* | 12/2016 | Djupesland ............ A61M 11/00 |
| 2017/0043109 A1 | 2/2017 | Hoekman et al. |
| 2017/0196861 A1 | 7/2017 | Cook et al. |
| 2018/0360110 A1* | 12/2018 | Marsot ................ A61M 15/009 |
| 2019/0000753 A1 | 1/2019 | Narasimha Murthy et al. |
| 2019/0001088 A1* | 1/2019 | Petit ...................... G01F 11/028 |
| 2019/0209463 A1 | 7/2019 | Hoekman et al. |
| 2019/0275036 A1 | 9/2019 | Haruta et al. |

FOREIGN PATENT DOCUMENTS

| | | |
|---|---|---|
| CN | 202263268 U | 6/2012 |
| CN | 203139302 U | 8/2013 |
| DE | 19518580 A1 | 11/1996 |
| DE | 102013100473 A1 | 7/2014 |
| EP | 0689438 A1 | 1/1996 |
| EP | 0865789 A3 | 1/1999 |
| EP | 1165044 A2 | 1/2002 |
| EP | 1165044 B1 | 6/2004 |
| GB | 806284 A | 12/1958 |
| GB | 1493614 A | 11/1977 |
| GB | 1517642 A | 7/1978 |
| JP | S 50-78912 A | 6/1975 |
| JP | H08322934 A | 12/1996 |
| JP | 2014-530637 A | 11/2014 |
| WO | WO 1986/001731 A1 | 3/1986 |
| WO | WO 9422445 A2 | 10/1994 |
| WO | WO 1999/013930 A1 | 3/1999 |
| WO | WO 2000/054887 A1 | 9/2000 |
| WO | WO 2001/036033 A2 | 5/2001 |
| WO | WO 2002/009707 A1 | 2/2002 |
| WO | WO 03/106840 A2 | 12/2003 |
| WO | WO-2005/025506 A3 | 3/2006 |
| WO | WO 2007/012853 A1 | 2/2007 |
| WO | WO 2007/081948 A2 | 7/2007 |
| WO | WO 2007/081948 A3 | 4/2008 |
| WO | WO 2008/059385 A2 | 5/2008 |
| WO | WO 2015/044782 A2 | 4/2015 |
| WO | WO 2017/044897 A1 | 3/2017 |
| WO | WO 2018/025089 A2 | 2/2018 |
| WO | WO 2019/008439 A1 | 1/2019 |

OTHER PUBLICATIONS

PCT International Search Report and Written Opinion, International Application No. PCT/US2016/051169, dated Jan. 26, 2017, 9 pp.

PCT International Preliminary Report on Patentability for PCT International Application No. PCT/US2016/051169, dated Mar. 29, 2018, six pages.

European Patent Office, Supplementary European Search Report, European Patent No. 16845229, dated Apr. 9, 2019, 8 pages.

The Patent Office of the People's Republic of China, First Office Action, CN Patent Application No. 201680060459.8, dated Apr. 14, 2020, 22 pages.

Japan Patent Office, Official Notice of Rejection, JP Patent Application No. 2018-513344, dated Apr. 7, 2020, nine pages.

Appasaheb, et al., "Review on Intranasal Drug Delilvery System", Journal of Advanced Pharmacy Education and Research, vol. 3, Issue 4, Oct. 2013, 14 pages.

Aurora, S. K. et al., "A Randomized, Double Blind, Placebo-Controlled Study of MAP0004 in Adult Patients With Migraine," Headache, Jun. 2009, pp. 826-837, vol. 49, No. 6.

Australian New Zealand Clinical Trials Registry, "A Phase I, Comparative Bioavailability Study of Dihydroergotamine Mesylate (DHE) Administered by I123 Precision Olfactory Delivery (PODTM) Device Nasal Spray, DHE for Injection (Intravenous), and Migranal® Nasal Spray in Healthy Male and Female adult Subjects," 2017, 7 pages.

Baron, "Orally Inhaled Dihydroergotamine; Reviving and Improving a Classic", Future Neurology, May 2011, 11 pages.

Constantino, et al., "Intranasal administration of acetylcholinesterase inhibitors", BMC Neuroscience, Dec. 10, 2008, 3 pages.

Cook, R. O. et al., "Reduced Adverse Event Profile of Orally Inhaled DHE (MAP0004) vs IV DHE: Potential Mechanism," Headache, Nov./Dec. 2009, pp. 1423-1434, vol. 49, No. 10.

"D.H.E. 45 (dihydroergotamine mesylate) Injection, USP," Valeant Pharmaceuticals North America, Aug. 2008, 16 pages.

European Patent Office, EP Office Action for 14727320.5, dated Nov. 9, 2016, 6 pages.

European Patent Office, EP Search Report for 09707800.0 dated Jul. 1, 2015, 12 pages.

European Patent Office, EP Search Report for 11818832.5 dated Sep. 24, 2014, 6 pages.

Hanson, et al., "Intranasal delivery of growth differentiation factor 5 to the central nervous system", Drug Delivery, 19(3):149-54, Feb. 2012, 7 pages.

Headache Classification Committee of the International Headache Society (IHS), "The International Classification of Headache Disorders, $3^{rd}$ edition," Cephalalgia, 2018, 211 pages, vol. 38, No. 1.

(56) References Cited

OTHER PUBLICATIONS

Hoekman, J.D., "The Impact of Enhanced Olfactory Deposition and Retention on Direct Nose-to-Brain Drug Delivery", UMI Dissertation Publishing, Apr. 11, 2011, 181 pages.
Humbert, H. et al., "Human pharmacokinetics of dihydroergotamine administered by nasal spray," Clinical Pharmacology & Therapeutics, Sep. 1996, p. 265-275, vol. 60, No. 3.
Impel Neuropharma, "Migraine Treatment," Apr. 29, 2016, three pages, [Online] [Retrieved on Jul. 19, 2017], Retrieved from the Internet <URL: http://web.archive.org/web/20160429165231/impelnp.com/migraine-treatment/>.
Impel Neuropharma, "POD Technology," Apr. 29, 2016, four pages, [Online] [Retrieved on Jul. 19, 2017], Retrieved from the Internet <URL: http://web.archive.org/web/20160429165242/http://impelnp.com:80/pod-technology/>.
Intellectual Property India Patent Application No. IN 201741000065, filed Jul. 2, 2017, Applicant: Dr. Reddy's Laboratories Limited.
Iwashima, F. et al., "STS101 (Dry Powder Intranasal Dihydroergotamine) Drug-Device Combination Achieves Consistent and Robust Delivery Performance for Migraine Patients," International Headache Conference, Sep. 5-8, 2019, one page.
Kellerman, D. J. et al., "Assessment of the Consistency of Absorption of Dihydroergotamine Following Oral Inhalation: Pooled results from Four Clinical Studies," Journal of Aerosol Medicine and Pulmonary Drug Delivery, 2013, pp. 297-306, vol. 26, No. 5.
Kumar, et al., "Nasal Drug Delivery: A Potential Route for Brain Targeting" The Pharma Innovation Journal, vol. 2, No. 1, Mar. 2013, 9 pages.
"Make the Most of MIGRANAL: Administration Instructions: How to Use MIGRANAL Nasal Spray," MIGRANAL Nasal Spray, Valeant Pharmaceuticals International, Inc., 2016, 7 pages.
Mauskop, A., "Getting medicine straight from the nose to the brain," Headache NewsBlog, Jan. 6, 2013, two pages, [Online] [Retrieved on Jun. 23, 2017], Retrieved from the Internet <URL: https://www.nyheadache.com/blog/getting-medicine-straight-from-the-nose-to-the-brain/>.
Mauskop, A., "Getting medicine straight from the nose to the brain," New York Headache blog, Jan. 6, 2013, 2 pages, [Online], [Retrieved Jun. 23, 2017], Retrieved from the Internet: <URL:https://www.nyheadache.com/blog/getting-medicine-straight-from-the-nose-to-the-brain/>.
"Migranal Product Label," Valeant Pharmaceuticals North America LLC, Nov. 2014, six pages.
NIH, "A Phase I Study to Study the PK and Safety of Single Doses of STS101, DHE Injection and Nasal Spray in Healthy Subjects," U.S. National Library of Medicine, ClinicalTrials.gov, Mar. 14, 2019, seven pages, [Online] [Retrieved on Dec. 24, 2019], Retrieved from the Internet <URL: https://clinicaltrials.gov/ct2/show/NCT03874832>.
NIH, "A Randomized, Double-Blind, Placebo-Controlled Study to Evaluate STS101 in the Acute Treatment of Migraine (EMERGE)," U.S. National Library of Medicine, ClinicalTrials.gov, Apr. 3, 2019, seven pages, [Online] [Retrieved on Dec. 24, 2019], Retrieved from the Internet <URL: https://clinicaltrials.gov/ct2/show/NCT03901482>.
Ozsoy, et al., "Nasal Delivery of High Molecular Weight Drugs", Molecules Journal, Sep. 23, 2009, 26 pages.
Parvathi, "Intranasal Drug Delivery to Brain: An Overview," published in the International Journal of Research in Pharmacy and Chemistry 2012, 2(3), 7 pages.
PCT International Search Report, PCT Application No. PCT/US/2009/033468 dated Dec. 2, 2009, 5 pages.
PCT International Search Report, PCT Application No. PCT/IB2014/002706, dated Mar. 20, 2015, four pages.
PCT Search Report and Written Opinion, PCT Application No. PCT/US2011/048435, dated Mar. 27, 2012, 14 pages.
PCT Invitation to Pay Additional Fees and, where Applicable, Protest Fee, PCT Application No. PCT/US2019/012405, Mar. 4, 2019, two pages.
Renner, et al., "Intranasal delivery of growth differentiation factor 5 to the central nervous system," Drug Delivery, Feb. 2012, 7 pages.
Saper, J. R. et al., "Pharmacology of Dihydroergotamine and Evidence for Efficacy and Safety in Migraine," Headache, Nov. 2006, pp. S171-S181, vol. 46, No. S4.
Shrewsbury, S. B. et al., "Intrapulmonary and intravenous administrations of dihydroergotamine mesylate have similar cardiovascular effects in the conscious dog," British Journal of Pharmacology, Jul. 2008, pp. 1254-1265, vol. 154, No. 6.
Shrewsbury, S. B. et al., "Randomized, double-blind, placebo-controlled study of the safety, tolerability and pharmacokinetics of MAP0004 (orally-inhaled DHE) in adult asthmatics," Current Medical Research and Opinion, 2008, pp. 1977-1985, vol. 24, No. 7.
Shrewsbury, S. B. et al., "Safety and Pharmacokinetics of Dihydroergotamine Mesylate Administered via a Novel (Tempo™) Inhaler," Headache, Mar. 2008, pp. 355-367, vol. 48, No. 3.
Shrewsbury, S. B. et al., STOP 101: A Phase 1, Randomized, Open-Label, Comparative Bioavailability Study of INP104, Dihydroergotamine Mesylate (DHE) Administered Intranasally by a 1123 Precision Olfactory Delivery (POD®) Device, in Healthy Adult Subjects, Headache, Mar. 2019, 16 pages, vol. 59, No. 3.
Shrewsbury, S.B. et al., "Intrapulmonary and intravenous administrations of dihydroergotamine mesylate have similar cardiovascular effects in the conscious dog," Nature Publishing Group, 2008, vol. 154, No. 6, 12 pages.
Shrewsbury, S.B., et al., "Safety, Tolerability and Comparative Bioavailability of a Novel Intranasal DHE Product (INP104)," Impel Neuropharma, American Headache Society 60th Annual Meeting, 2018, 1 page.
Silberstein, S.D. et al., "Dihydroergotamine: a review of formulation approaches for the acute treatment of migraine," CNS Drugs, 2013, p. 385-394, vol. 27, No. 5.
Silberstein, S. D. et al., "Dihydroergotamine (DHE)—Then and Now: A Narrative Review," Headache, 2019, 18 pages.
Silberstein, S.D., et al., "Ergotamine and dihydroergotamine: history, pharmacology, and efficacy," Headache: The Journal of Head and Face Pain, 2003, vol. 43, No. 2, pp. 144-166.
Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, 2011, vol. 39, No. 12, 8 pages.
Strom, S. et al., "Comparison of the Pharmacokinetics of STS101, an Intranasal Dry Power Formulation of Dihydroergotamine, with Other Intranasal, Injectable, and Oral Inhaled DHE Formulations," International Headache Conference, Sep. 5-8, 2019, one page.
Talegaonkar, et al., "Intranasal delivery: an approach to bypass the blook brain barrier", Indian J Pharmacol, Jun. 2004, vol. 36, Issue 3, 8 pages.
Van Der Kuy, P-H. M. et al., "Bioavailability of intranasal formulations of dihydroergotamine," European Journal of Clinical Pharmacology, Nov. 1999, pp. 677-680, vol. 55, No. 9.
Wang, Y. et al., Abstract of "Brain uptake of dihydroergotamine after intravenous and nasal administration in the rat," Biopharm Drug Dispos., Dec. 1998, two pages, [Online] [Retrieved on Jul. 18, 2017], Retrieved from the Internet <URL: https://pubmed.ncbi.nlm.nih.gov/9872338/>.
Westin et al, "Direct Nose to Brain Transfer of Morphine After Nasal Administration to Rats", Pharmaceutical Research, vol. 23, No. 3, Mar. 2006, 8 pgs.
Westin, "Olfactory Transfer of Analgesic Drugs After Nasal Administration", Digital Comprehensive Summaries of Uppsala Dissertations from the Faculty of Pharmacy 55, May 11, 2007, 66 pages.
Yamada, et al., "Nose-to-brain delivery of TS-002, prostaglandin D2 analogue", Journal of Drug Targeting, Jan. 2007, 9 pages.
Yimam, et al., "Effects of lipid association on lomustine (CCNU) administered intracerebrally to syngeneic 36B-10 rat brain tumors", Cancer Letters 244(2), Dec. 2006, 9 pages.
Ying, "The nose may help the brain: intranasal drug delivery for treating neurological diseases" Future Medicine, 3(1), Jan. 2008, 4 pages.
Zhang, et al, "The brain targeting efficiency following nasally applied MPEG-PLA nanoparticles in rats", Journal of Drug Targeting, Jun. 2006, 11 pages.

(56) References Cited

OTHER PUBLICATIONS

China National Intellectual Property Administration, Notice of Allowance, Chinese Patent Application No. 201680060459.8, dated May 8, 2021, three pages (with concise explanation of relevance).
China National Intellectual Property Administration, Search Report, Chinese Patent Application No. 201680060459.8, dated Apr. 15, 2021, six pages.
Djupesland, G., "Nasal drug delivery devices: characteristics and performance in a clinical perspective—a review," Drug Delivery and Translational Research, 2013, pp. 42-62, vol. 3.
Righton, L., "Nasal MDIs—moving beyond nasal allergy," manufacturing chemist, Sep. 2014, pp. xi-xiii.

* cited by examiner

A    B    C

IN-LINE NASAL DELIVERY DEVICE

CROSS REFERENCE TO RELATED APPLICATION

This application claims priority to U.S. Provisional Patent Application No. 62/216,789 filed Sep. 10, 2015, the contents of which are hereby incorporated by reference herein in their entirety.

BACKGROUND

Depositing drug on the olfactory region of the nasal cavity is difficult to accomplish due to the complex architecture of the nasal cavity and the turbinate guided air path for inhaled breath through the nose. These natural structures act to prevent materials from depositing on the olfactory region as a way to protect this entry way into the central nervous system (CNS). Nasal drop or spray devices, such as the Pfieffer nasal spray devices (Radolfzell, Germany), are designed to saturate the lower nasal cavity. Drug deposited on the lower nasal cavity is absorbed into the blood stream instead of the CNS, eliminating an advantage of using the nasal route for CNS delivery.

A more elegant approach to the intranasal delivery of compounds or mixtures is needed.

SUMMARY

Shown and described is one implementation of a device for the intranasal delivery of a compound including a y-junction having a base, a first branch of the y-junction radiating from the base, a second branch of the y-junction radiating from the base, a third branch of the y-junction radiating from the base, and an internal dose loading channel of the y-junction, a metered dose pump in fluid communication with the first branch of the y-junction, a conical spring associated with the second branch of the y-junction, a dose chamber in fluid communication with the third branch of the y-junction, a nozzle associated with the dose chamber, a diffuser compression fit between the internal dose loading channel and the dose chamber, an actuator grip surrounding the y-junction, and a housing, the y-junction residing within the housing.

In one aspect, the in-line nasal delivery device further includes a propellant canister in fluid communication with the second branch of the y-junction and held by the actuator grip, the conical spring between the propellant canister and the second branch of the y-junction.

In another aspect, the in-line nasal delivery device further includes a vial in fluid communication with the metered dose pump.

In yet another aspect, the in-line nasal delivery device further includes a pump fitment securing the metered dose pump to the vial.

In another implementation, shown and described is an in-line nasal delivery device for the intranasal delivery of a compound including a housing, the housing including a tip, an actuator, and a dose chamber, the tip and the dose chamber in fluid communication within the housing, a nozzle at a distal portion of the tip, the nozzle providing an outlet for the compound, and a pump in fluid communication with the dose chamber, the pump to move the compound into the dose chamber.

In one aspect, the in-line nasal delivery device further includes a propellant canister in communication with the housing, the propellant canister having a propellant valve and in fluid communication with the dose chamber.

In another aspect, the in-line nasal delivery device further includes a vial of compound cooperative with the pump to move the compound into the dose chamber.

In another aspect, the in-line nasal delivery device when actuated compresses the pump moving the compound into the dose chamber and actuation of the propellant valve disperses the propellant pushing the compound providing for the compound to exit the device through the nozzle openings.

The invention will best be understood by reference to the following detailed description of various implementations, taken in conjunction with any accompanying drawings. The discussion below is descriptive, illustrative and exemplary and is not to be taken as limiting the scope defined by any appended claims.

DESCRIPTION OF THE DRAWINGS

The foregoing aspects and many of the advantages will be more readily appreciated as the same become better understood by reference to the following detailed description, when taken in conjunction with the accompanying drawings, wherein:

FIG. 2A shows the in-line nasal delivery device at rest with FIG. 2B showing the actuation of the pump and FIG. 2C showing actuation of the propellant valve.

DETAILED DESCRIPTION

When trade names are used herein, applicants intend to independently include the trade name product and formulation, the generic compound, and the active pharmaceutical ingredient(s) of the trade name product.

For clarity of disclosure, and not by way of limitation, the detailed description is divided into the subsections which follow.

Unless defined otherwise, all technical and scientific terms used herein have the same meaning as commonly understood by one of ordinary skill in the art pertinent to the methods, apparatus and compositions described. As used herein, the following terms and phrases have the meanings ascribed to them unless specified otherwise:

"A" or "an" may mean one or more.

In one implementation, the in-line nasal delivery device 1 delivers compound into the nasal cavity and deposits compound in the nasal cavity beyond the nasal valve. The deposition includes the turbinates and/or the olfactory region. The compound delivered is a liquid. The compound may be a drug, active pharmaceutical ingredient, or a pharmaceutical formulation. The compound delivered may be a dose.

Figure 1:
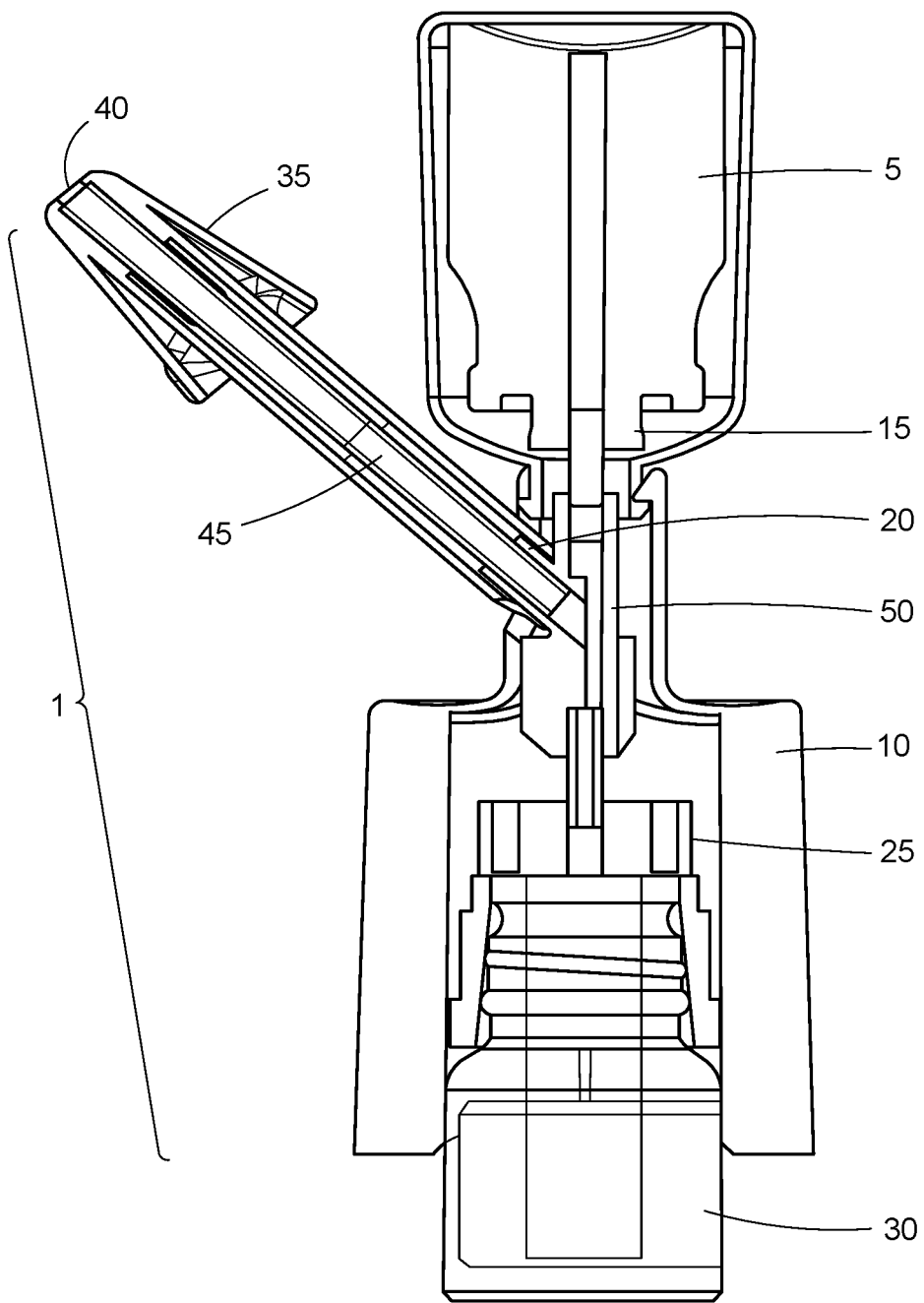
FIG. 1 shows a cross section of the in-line nasal delivery device.

As shown in FIG. 1, the in-line nasal delivery device 1 includes a housing 10, diffuser 20, tip 35, nozzle 40, dose chamber 45, an actuator 50, and a pump 25 to move the compound into the dose chamber 45. In one aspect, the in-line nasal device 1 is associated and cooperative with a propellant canister 5, a propellant valve 15, and a vial 30 of compound cooperative with the pump 25 to move the compound into the dose chamber 45.

In one aspect, the diffuser 20 is a frit. The diffuser provides for the conversion of the liquefied propellant in the propellant canister 5 to gas and/or an increase in temperature of the propellant.

In one aspect, the propellant valve 15 is a metered dose propellant valve.

In one aspect, the compound is supplied in the form of a sealed vial 30, e.g., of glass, that contains a quantity of liquid. In one aspect, the vial 30 has a neck that is sealed by a removable closure (not shown), for example but not limited to sealed with a plastic cover, crimped metal seal, and rubber stopper (for stability and sterility purposes). In one aspect, the vial 30 may contain the active pharmaceutical ingredient. When the closure is removed, the device 1 is engaged with the vial 30, in one aspect, by cooperation with the neck of the vial 30. A pump 25 moves the compound into the dose chamber 45.

The propellant canister 5 is a canister of a compressed gas or a liquefied propellant. Compressed gases include but are not limited to compressed air and compressed hydrocarbons. In one aspect, nitrogen or carbon dioxide. Liquefied propellants include but are not limited to chlorofluorocarbons and hydrofluoroalkanes. The canister 5 will generally be provided with a propellant valve 15 by which the gas flow can be controlled.

The tip 35 includes a nozzle 40. In one aspect, the nozzle 40 has a plurality of nozzle openings (not shown). Thru the plurality of nozzle openings, the compound and propellant is delivered to the nasal cavity.

Figure 2:
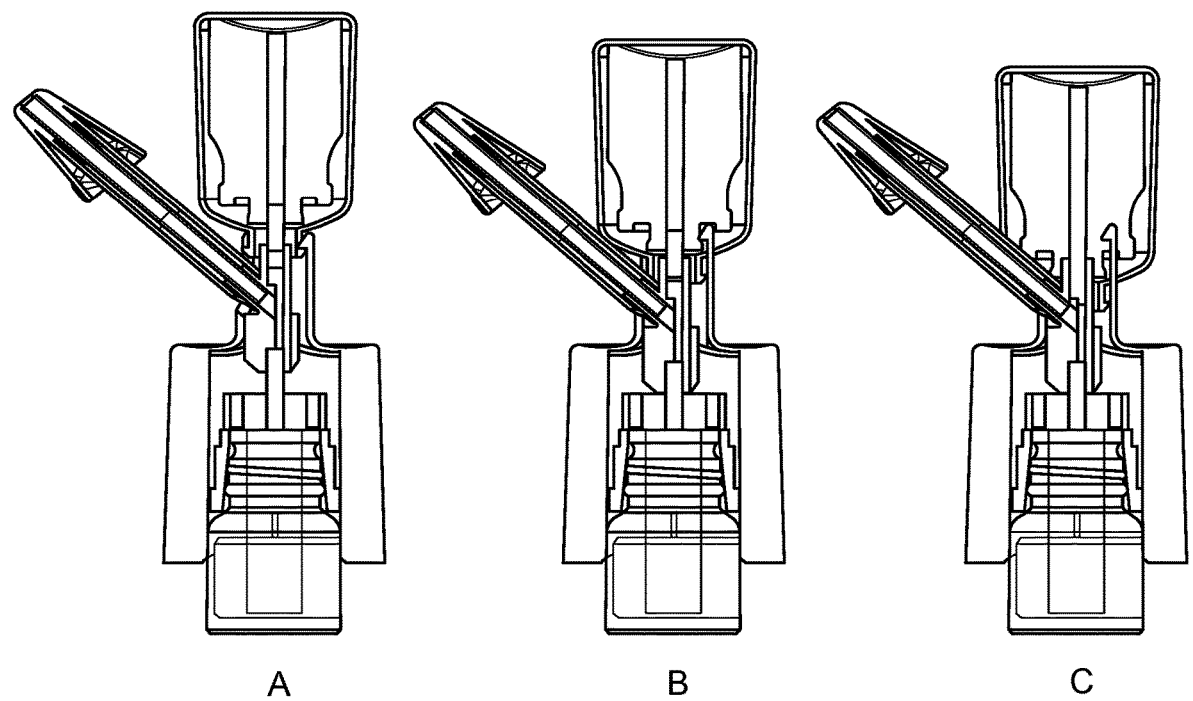
FIG. 2 shows a cross section of the in-line nasal delivery device in the stages of rest and actuation.

Actuation of the propellant canister 5 is effectively coordinated with actuation of the pump 25 for the vial 30 for the compound. The arrangement may be such that actuation of the vial 30 for the compound causes actuation of the propellant canister 5. FIG. 2 shows the device 1 at rest (FIG. 2A) and in actuation (FIGS. 2B and 2C).

As an example, the staging of the device 1 actuation is as follows. The housing 10 is compressed to prime the propellant canister 5. When the housing 10 is compressed, an actuator 50 remains stationary in the housing 10 while the propellant canister 5 and the vial 30 move towards the actuator 50. At this time, the propellant valve 15 associated with the propellant canister 5 is not actuated by compression. The actuator 50 acts upon the pump 25 compressing the pump 25 and the compound from the vial 30 is moved into the dose chamber 45. After a majority of the compound has moved into the dose chamber 45, the actuator 50 acts upon the propellant valve 15 and the propellant valve 15 begins to compress. The continued depression of the actuator 50 releases the propellant from the propellant canister 5. The propellant pushes the compound as it exits the device 1 through the nozzle openings 41 of the nozzle 40 located in the tip 35. The actuator 50 provides for first actuation of the pump 25, then once the pump 25 bottoms out, the continued depression of the actuator 50 provides for release of the propellant from the canister 5.

In an alternative implementation of the device 1 (not shown), the device 1 does not include a diffuser 20.

Figure 3:
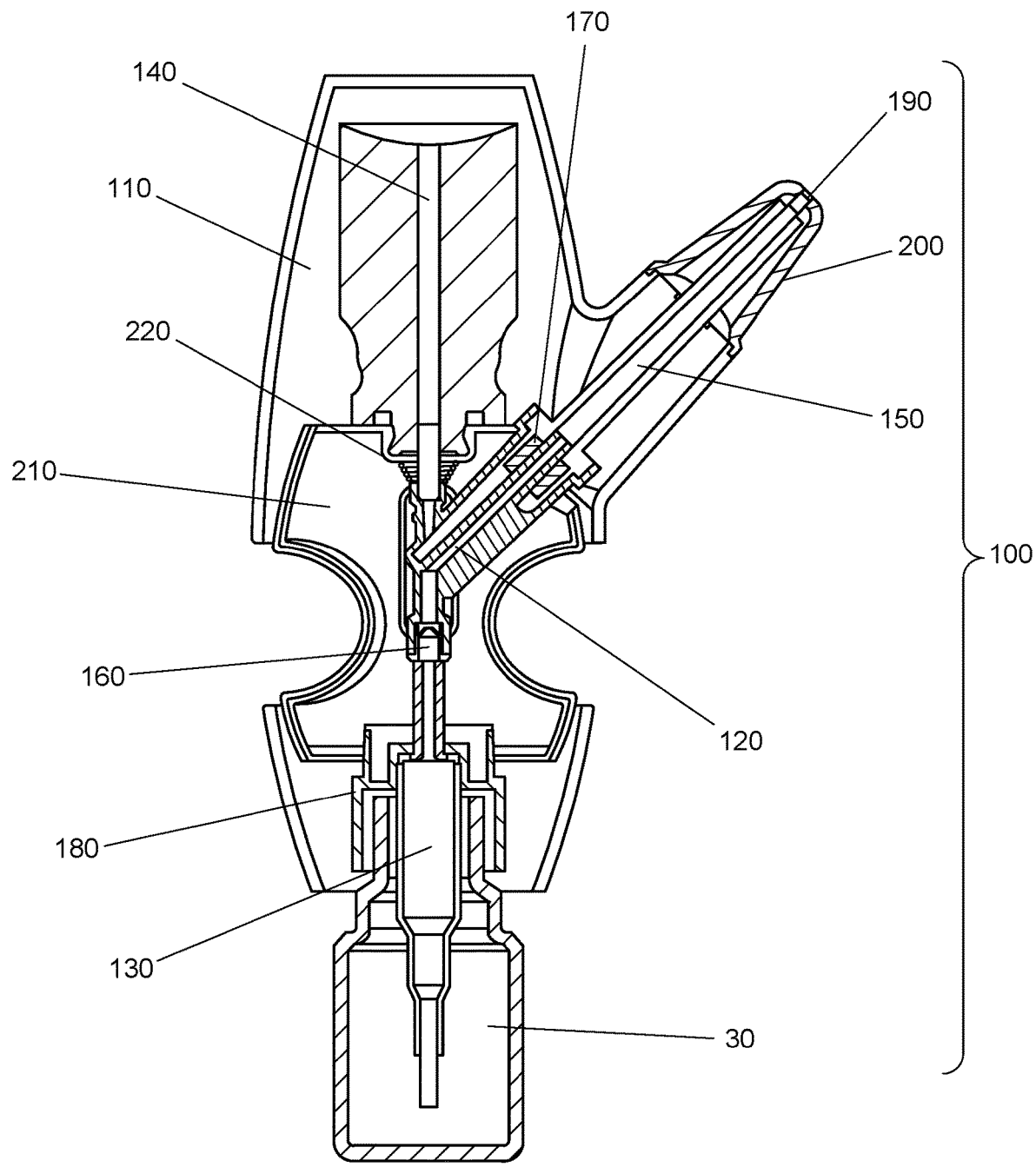
FIG. 3 shows a cross section of another implementation of the in-line nasal delivery device.

FIG. 3 shows yet another implementation of the device 100. The device 100 can deliver a single or multiple dose from a vial 30 or other container. For example, the vial 30 may contain a volume of compound for multiple doses, while the user may decide to only deliver a single dose from the vial 30. The compound may be a drug, active pharmaceutical ingredient, or a pharmaceutical formulation.

Initially, the vial 30 may be separate from the rest of the assembled device 100. At the time of use, the device 100 and vial 30 are taken out of their respective packaging. Prior to use, the vial 30 will generally be sealed. In the aspect where the vial 30 is covered by a plastic cover, metal seal and stopper, the plastic cover and metal seal are pulled away from the top of the vial 30, and the rubber stopper is removed from the vial 30. The vial 30 may be screwed into a pump fitment 180 located at the base of the device 100. For example, but not limited to, the vial 30 may have female threads which can be screwed into male threads on a pump fitment 180, or vice versa. The vial 30 may contain, for example but not limited to, inclusive of end points, 2-3 ml, in another aspect 2-2.5 ml of compound.

As shown in FIG. 3, the device 100 includes a housing 110. The housing 110 contains components of the device 100 including the y-junction 120. The y-junction 120 has three branches radiating from a common base. The y-junction and its three branches may be a molded component. The y-junction 120 establishes both fluid and gas paths within the device 100, and connects the metered dose pump 130, the dose chamber 150, and the propellant canister 140 when the propellant canister 140 is assembled with the device.

As shown in FIG. 3, for use of the device 100, the user will generally orient the device 100 with the propellant canister 140 assembled and located at the top and the vial 30 assembled and located at the bottom. Housed within the device's 100 housing 110, the optional check-valve 160 (attached to the metered dose pump 130 stem) press fits into a receiving hub of a first branch of the y-junction 120. An internal bore provides fluid communication from the metered dose pump 130, through the optional check-valve 160 and y-junction 120, to the dose chamber 150. In one aspect, the check valve 160 is an elastomeric component that installs within a plastic housing between the metered dose pump 130 and the y-junction 120. The optional check valve 160: (a) reduces or eliminates dose leakage which could occur through the metered dose pump 130 if the pump stem was depressed and the propellant canister 140 was actuated; (b) allows for improved consistency in dose delivery by the device 100; and/or (c) provides that compound is not pushed back down the internal dose loading channel 230 of the y-junction 120 and into the metered dose pump 130.

When oriented as to be used in operation, housed within the device's 100 housing 110, towards the top of the device 100, the propellant canister 140 press fits into a second branch of the y-junction 120, establishing the gas path through internal bores, through the diffuser 170 and to the dose chamber 150.

Figure 4:
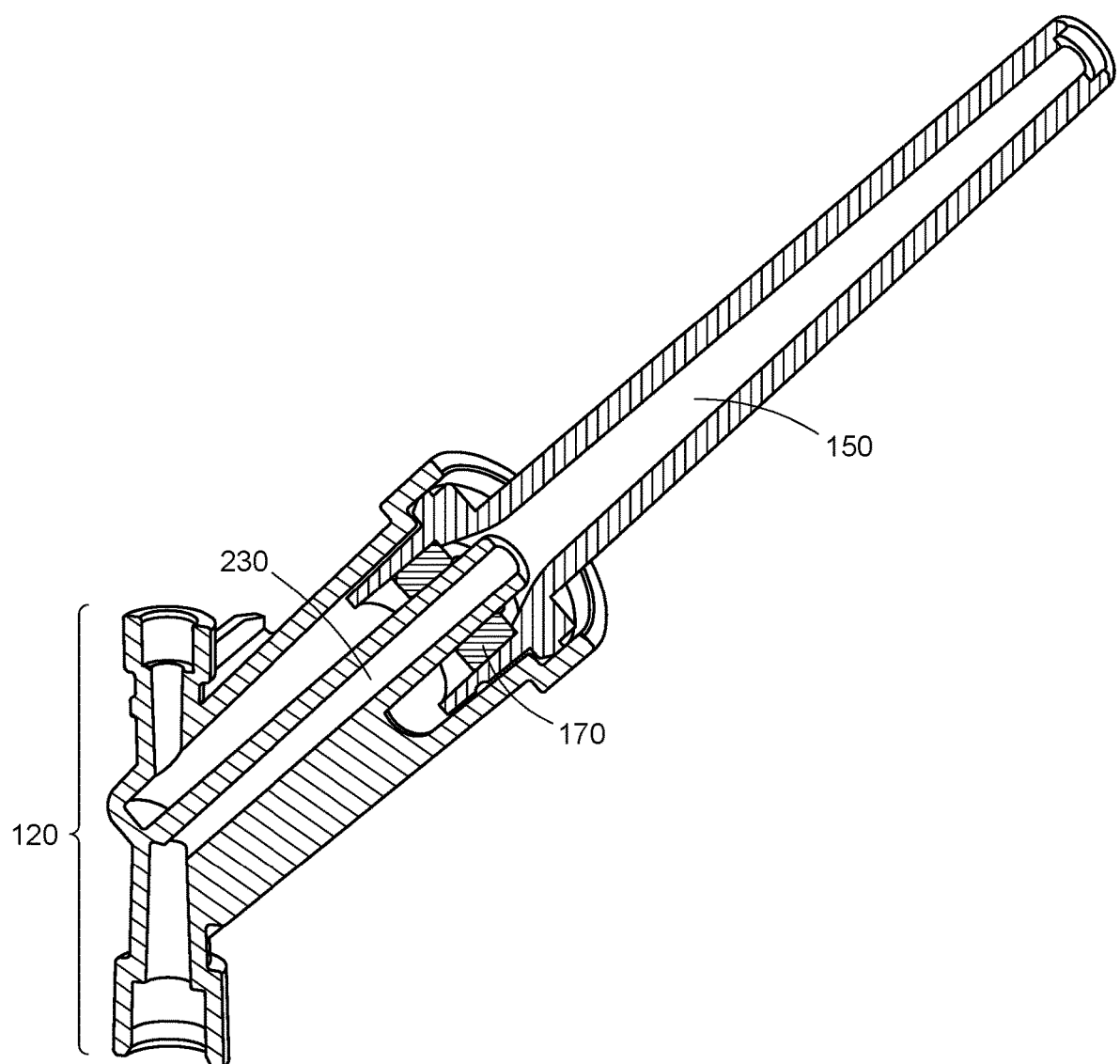
FIG. 4 shows a cross section of the diffuser as seated within the device.

In this implementation of the device 100, the diffuser 170 is annular. As shown in FIG. 4, the annular diffuser 170 sits inside a bore on the back end of the dose chamber 150. The external diameter of the annual diffuser 170 is in a compression fit with the dose chamber 150. An internal dose loading channel 230 which is molded as a portion of the y-junction 120 fits into the inner bore of the annual diffuser 170 when the dose chamber 150 is installed onto the y-junction 120. The inner diameter of the annular diffuser 170 is in compression with the internal dose loading channel 230 portion of the y-junction 120. The annular diffuser 170 is seated between the outer wall of the internal dose loading channel 230 and the inner wall of the dose chamber 150, sealing against both of those surfaces to form the bottom of the dose chamber 150.

In one aspect, the diffuser 170 is a frit. The diffuser 170: (a) provides for the conversion of the liquefied propellant in the propellant canister 140 to gas; (b) provides an increase in temperature of the propellant; (c) acts to prevent the propellant from flowing back into the device 100; (d) acts to prevent the compound from flowing back into the device 100; and/or (e) acts to allows gas flow into the dose chamber 150 while preventing the compound from leaking out. The diffuser may be made of a porous polymer material.

Figure 6:
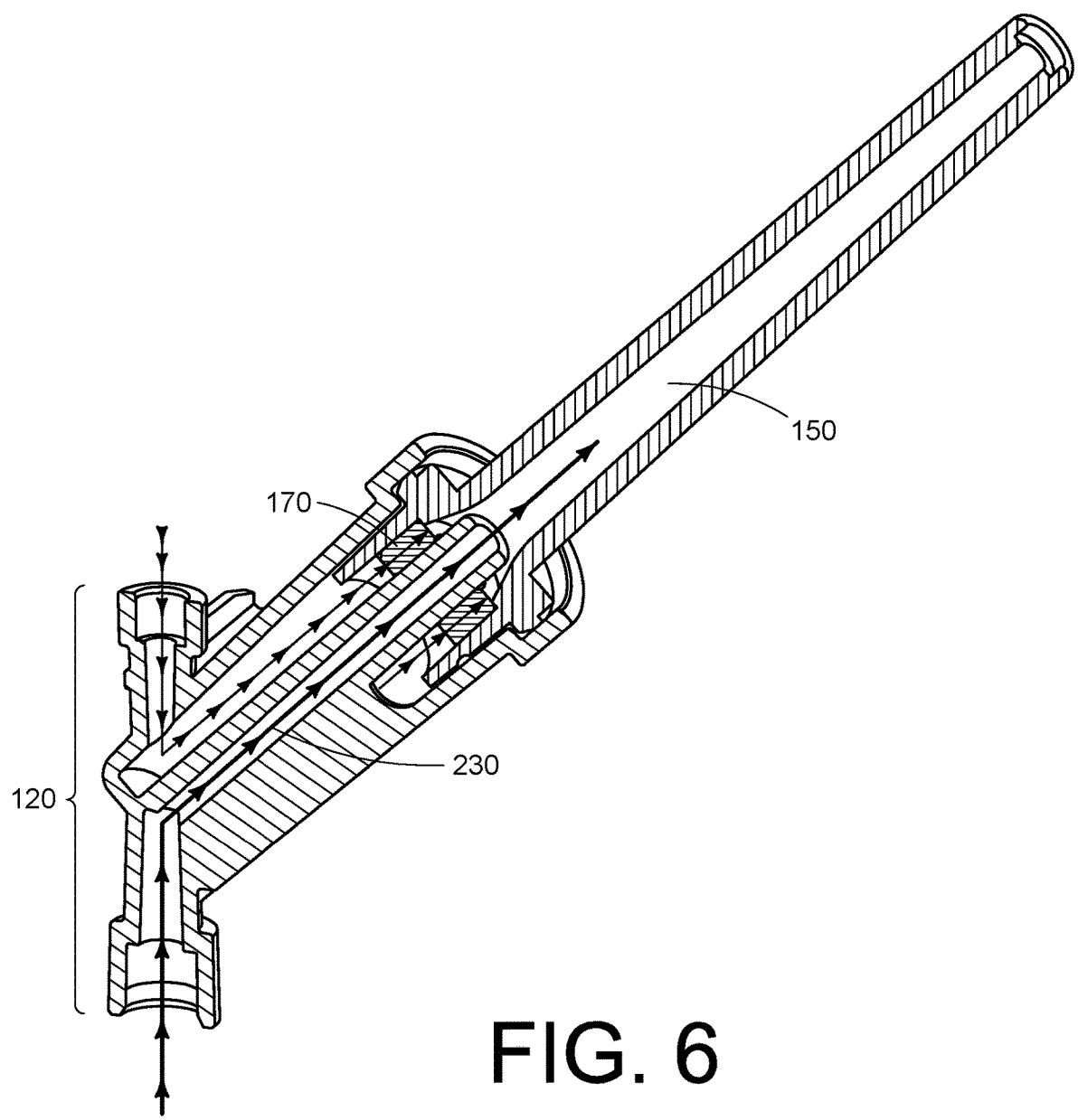
FIG. 6 shows arrows representing both dose and propellant flow.
Figure 7:
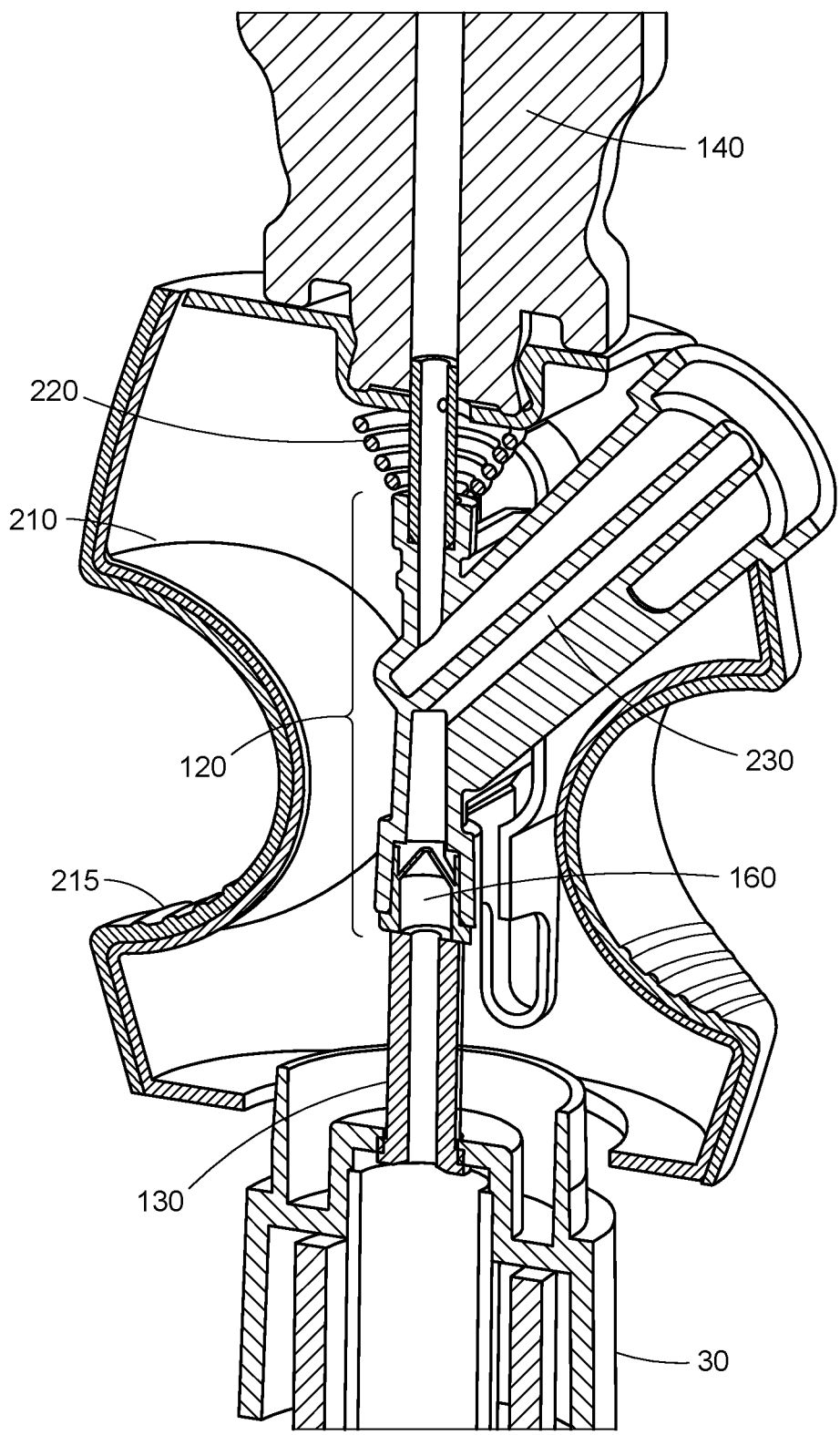
FIG. 7 shows the actuator grip and conical spring arrangement.
Figure 8:
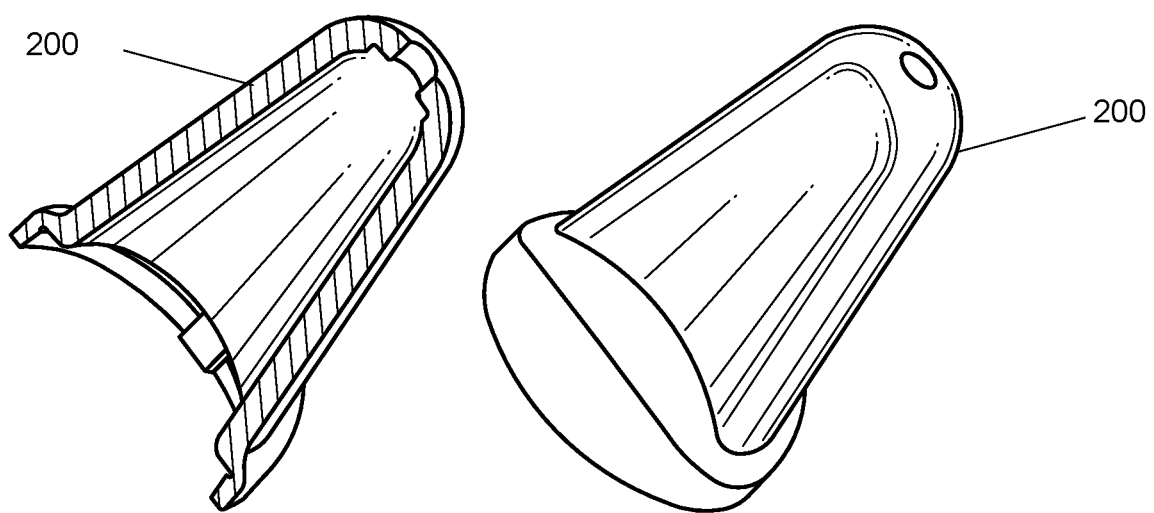
FIG. 8 shows a cross section of the optional nose cone and a side elevation of the optional nose cone.

The relationship in operation of the device 100 between the compound, the annular diffuser 170, the inner dose loading tube 230, the dose chamber 150 and the y-junction 120 are shown at least in FIG. 6. In operation, the compound being loaded into the dose chamber 150 takes the less restrictive route, flowing out of the vial 30 and filling the dose chamber 150 rather than loading backwards through the annular diffuser 170 and into the delivery path of the propellant of the y-junction 120. In operation of the device 100, the staging of operation and the amount of time required for operation of the device allows the annular diffuser 170 to restrict compound from flowing back into the y-junction 120 for the period of time needed, as the propellant canister 140 is activated after compound loading. During proper device 100 use, the entire actuation of the device 100, including metered dose pump 130 and propellant canister 140, is approximately a second or less than a second. The loaded dose in the dose chamber 150 does not have enough time to flow backwards into the y-junction 120. Immediately after the dose chamber 150 is full, the propellant expels the compound from the device 100.

On the third leg of the y-junction 120 at a 45-degree angle, the dose chamber 150 press fits into the y-junction 120, completing the flow paths for both gas and fluid through the device. In one aspect, the angle is 30 degrees, 35 degrees, 40 degrees, 45 degrees, 50 degrees, 55 degrees, 60 degrees, inclusive of endpoints and intervening degrees.

The y-junction 120 may contain engagement ribs (not shown) to help secure and position the assembly within the housing 110 of the device 100.

The device 100 includes a pump fitment 180. The pump fitment 180 secures the metered dose pump 130 to the vial 30 and holds both components in place during device 100 use. One aspect of the pump fitment 180 is that it consists of engagement ribs that retain it within the housing 110, provide vertical displacement, and prevent rotation during installation of the vial 30.

Figure 5A:
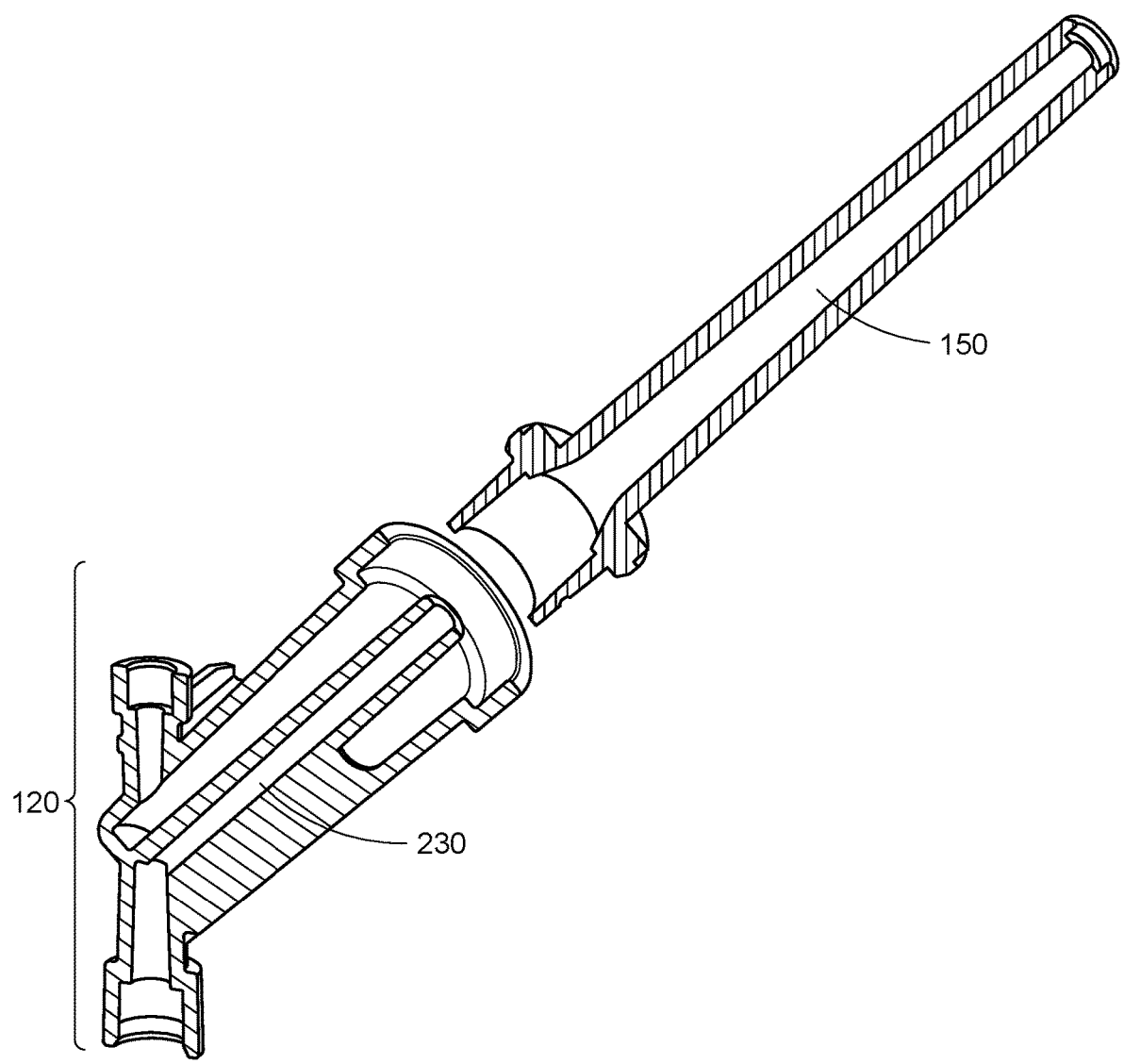
FIG. 5A shows an exploded view of the dose chamber and the y-junction unassembled.
Figure 5B:
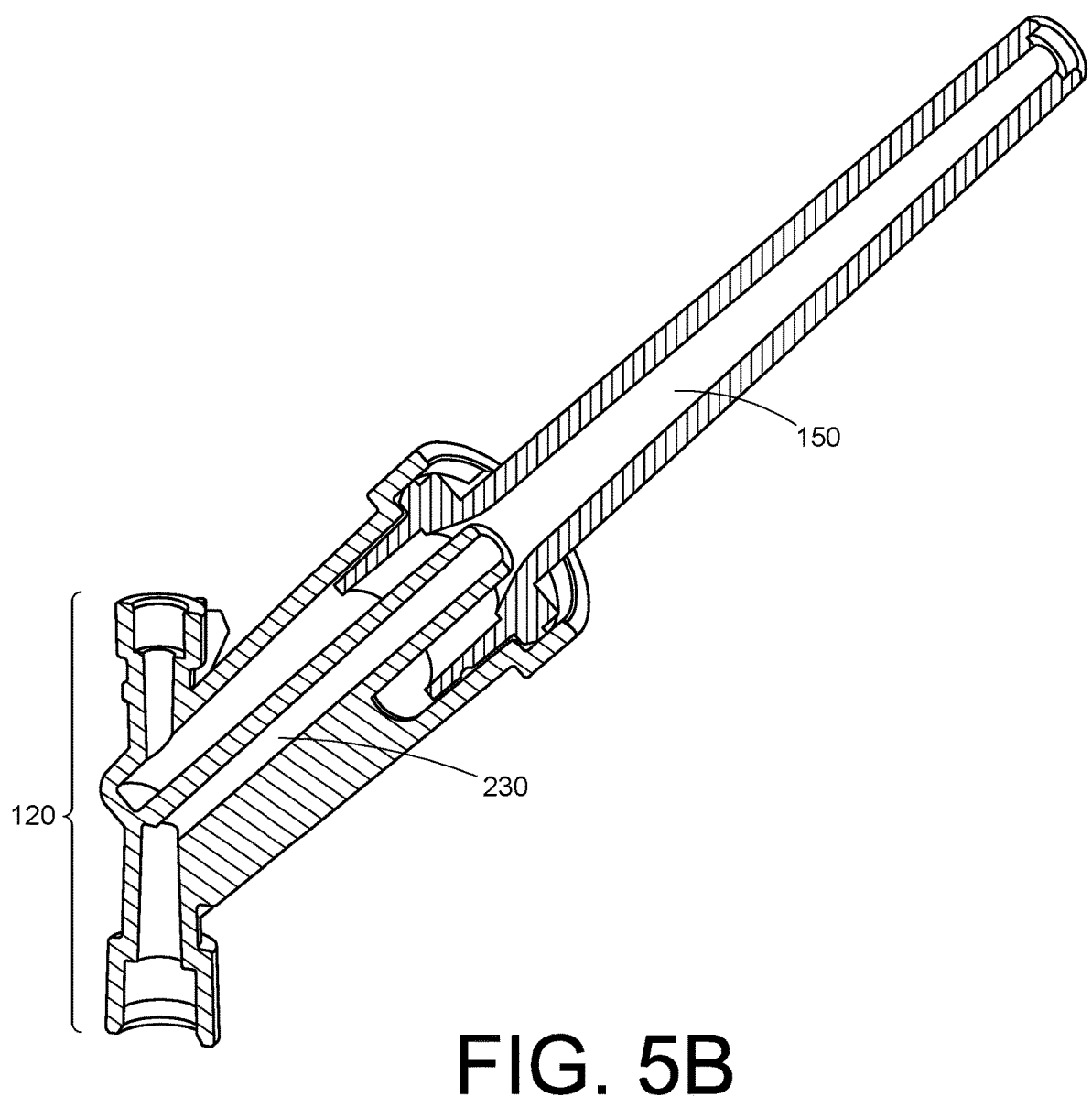
FIG. 5B shows an exploded view of the dose chamber and y-junction in cooperation.

The device 100 includes a dose chamber 150. The dose chamber 150 receives and stores the compound that has been pushed out of the inner tube of the y-junction 120. When the propellant canister 140 is actuated, the y-junction 120 and dose chamber 150 are pressurized and the propellant gas expels the compound out of the dose chamber 150. As shown in FIGS. 5A and 5B, the dose chamber 150 is press fit into the y-junction 120. The nozzle 190 is installed into the end of the dose chamber 150 opposite where it is press fit into the y-junction 120.

The nozzle 190 is installed into the distal end (end opposite where the dose chamber 150 is press fit into the y-junction 120) of the dose chamber 150, forming a liquid and gas-tight seal around the outer diameter. During actuation of the device 100, propellant evacuates liquid compound from the dose chamber 150, pushing it out the nozzle 190.

The nozzle 190 forms the narrow plume angle (for example, an angle of 1 to 40 degrees, including endpoints and angles intermittent there between; in one aspect the angle is 5 degrees, 10 degrees, 15 degrees, 20 degrees, 25 degrees, 30 degrees, 35 degrees) multi-stream deposition. The nozzle 190 and resultant angle of the plume produced promotes delivery of the compound to the olfactory region of the user's nasal cavity.

In this implementation, as shown in FIG. 8, the device 100 may include an optional nose cone 200. The external geometries of the nose cone 200 assist in providing proper alignment of the device 100 during insertion into the nose. The diametrically opposed flat sides aid with placement against the septum of either naris, with the depth stop providing correct depth of insertion. The nose cone 200 adds redundancy to nozzle 190 retention through mechanical interference incorporated into the design. As shown in FIG. 3 and FIG. 8, there is an opening in the nose cone 200 which aligns with the nozzle 190. The nose cone 200 is not part of the pressurized flow path.

The housing 110 represents the body of the device 100. The housing 110 includes two different "clamshells" concealing the components of the device 100 and retaining all components to ensure functionality. The housing 110 houses the metered dose pump 130 and pump fitment 180, the actuator grip 210, the y-junction 120, the propellant canister 140, and the dose chamber 150. The nose cone 200 engages onto the outer geometry of the housing 110. The housing 110 is designed to assemble easily through the use of, for example but not limited to, mattel pins, snaps, post or screws, or a combination thereof, molded into the geometry.

The actuator grip 210 provides for actuation displacement by the user. The actuator grip 210 is composed of two parts, and surround the y-junction 120 and reside within the housing 110. FIG. 7 shows two finger grip notches 215 are designed into the actuator rip 210 to allow the user to engage the device 100 with the fingers, for example but not limited to, the index and middle finger. These finger grip notches 215 allow the user to apply downward movement leading to device 210 actuation.

The metered dose pump 130 draws compound up from the vial 30 to the y-junction 120. The metered dose pump 130 may utilize a custom pump fitment 180 to promote functionality within the device 100, and allow attachment of the vial 30 via threads. The metered dose pump 130 may deliver, for example but not limited to, volumes, 180 μl, 200 μl, or 230 μl during actuation. Commercially available metered dose pumps 130 can be used.

For the device 100 to consistently deliver compound, the metered dose pump 130 must first deliver compound, followed by propellant canister 140 actuation to expel the compound. As shown in FIG. 7, one manner in which to accomplish this is via a conical spring 220 between the propellant canister 140 and y-junction 120 to create the necessary propellant canister 140 actuation force resulting in the correct order of actuation between the metered dose pump 130 and propellant canister 140. In one implementation, a conical spring 220 is used, although this force is not limited to being produced by a conical spring 220 as other mechanisms can be used. In one aspect, the conical spring 220 has a near zero preload, with a k value of about 25.5 lbf/in and a maximum load of 3.2 lbf. Selection of the spring or mechanism will include the considerations of: (a) providing for proper device 100 staging; (b) physical space in the device 100; and/or (c) and user feedback regarding how stiff of a conical spring 220 still allows a variety of users to activate the device 100.

The conical spring 220 is installed inline between the propellant canister 140 and y-junction 120. The actuator grip 210 physically holds the propellant canister 140. The user activates the device 100 by, for example, applying an in-line force acting down from the actuator grips 210, and up from the vial 30. This force simultaneously acts to activate both the metered dose pump 130 and the propellant canister 140. The conical spring 220 acts in parallel to the internal propellant canister spring, increasing the necessary force required to activate the propellant canister 140. By choosing the conical spring 220 such that the necessary force required to actuate the propellant canister 140 is in excess of the maximum necessary force required to completely actuate the metered dose pump 130, the device 100 provides that dose is loaded into the dose chamber 150 before propellant gas begins to expel compound from the device 100.

During device 100 actuation, the metered dose pump 130 draws liquid compound up from the vial 30 at the bottom of the device 100 via the y-junction 120, through the internal dose loading channel 230 and into the dose chamber 150. The internal dose loading channel 230 provides a clear route for the compound to be loaded ahead of the annular diffuser 170, without needed to physically pass through the porous material of the annular diffuser 170. As shown in FIG. 6, small arrow heads represent the flow of the propellant while large arrow heads represent the flow of the compound. Priming shots may be required to completely fill the metered dose pump 130 and internal dose loading channel 230 of the y-junction 120 prior to user dosing. A dose cap (not shown) may cover the nose cone 200 of the device 100 and captures the priming shots while also providing a means of visual indication to the user that the device is primed.

In the second stage of device 100 actuation, once the dose chamber 150 has been filled, the propellant canister 140 releases propellant which enters through the top of the y-junction 120, following the path shown by open arrow heads in FIG. 6. The propellant flows physically through the porous material of the annular diffuser 170, which promotions in the vaporization of the propellant. The propellant first contacts the compound at the distal (distal being closer to the nozzle 190, proximal being farther away from the nozzle 190) face of the annular diffuser 170 as seated in the device 100. As the propellant continues to expand, it pushes the compound forward (toward the nozzle 190) in the dose chamber 150, exiting though the nozzle 190 at the end of the dose chamber 150.

The propellant canister 140 provides the propulsive energy for the device 100. The stem of the propellant valve seats into the top receiver of the y-junction 120. During use, the user presses down on the actuator grips 210 which pulls the propellant canister 140 body down, actuating the propellant valve. This releases a metered volume of liquid propellant. As the propellant vaporizes and expands, the compound is forced out of the dose chamber 150 and out through the nozzle 190.

As an example of propellant, but not limited to, the propellant canister 140 uses HFA 134A as the propellant for the system. Other propellants are envisioned. There are commercially available propellant canisters 140.

The device 100, the propellant canister 140, and the vial 30 may all be included or provided together in a kit.

EXAMPLES AND EMBODIMENTS

Example 1

The following table provides data on one implementation of the device described herein.

| | Dose Volume [µL] | | | | | |
|---|---|---|---|---|---|---|
| Shot # | Device 1 | Device 2 | Device 3 | Device 4 | Device 5 | Device 6 |
| 1 | 190.6 | 193.7 | 185.3 | 199.2 | 199.2 | 145.1 |
| 2 | 181.4 | 205.5 | 178.9 | 167.7 | 167.7 | 141.7 |
| 3 | 183.1 | 188.5 | 173.3 | 165.6 | 165.6 | 138.5 |
| 4 | 183.2 | 193.3 | 145.8 | 164.6 | 164.6 | 136.6 |
| 5 | 183.3 | 201.5 | 200.7 | 162.0 | 162.0 | 142.1 |
| 6 | 185.8 | 207.7 | 166.3 | 179.4 | 179.4 | 138.9 |
| 7 | 184.3 | 195.1 | 180.3 | 164.8 | 164.8 | 140.9 |
| 8 | 183.3 | 205.4 | 175.3 | 164.9 | 164.9 | 142.0 |
| 9 | 180.5 | 178.1 | 172.0 | 164.1 | 164.1 | 141.8 |
| 10 | 179.7 | 204.0 | 178.0 | 170.6 | 170.6 | 143.9 |
| Mean | 183.5 | 197.3 | 175.6 | 170.3 | 170.3 | 141.2 |
| StDev | 3.1 | 9.3 | 14.0 | 11.3 | 11.3 | 2.5 |
| Min | 179.7 | 178.1 | 145.8 | 162.0 | 162.0 | 136.6 |
| Max | 190.6 | 207.7 | 200.7 | 199.2 | 199.2 | 145.1 |

185 uL + 10% 203.5
185 uL − 10% 166.5
185 uL + 15% 212.8
185 uL − 15% 157.3

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A device for the intranasal delivery of a compound comprising:
a y-junction including a base, a first branch of the y-junction radiating from the base, a second branch of the y-junction radiating from the base, a third branch of the y-junction radiating from the base, and an internal dose loading channel of the y-junction;
a metered dose pump in fluid communication with the first branch of the y-junction;
a conical spring associated with the second branch of the y-junction;
a dose chamber in fluid communication with the third branch of the y-j unction;
a nozzle associated with the dose chamber;
a diffuser between the internal dose loading channel and the dose chamber;
an actuator grip surrounding the y-junction; and
a housing, the y-junction residing within the housing.

Clause 2. The device of any of clauses 1-11, further comprising:
a propellant canister in fluid communication with the second branch of the y-junction and held by the actuator grip, the conical spring between the propellant canister and the second branch of the y-junction.

Clause 3. The device of any of clauses 1-11, further comprising a vial in fluid communication with the metered dose pump.

Clause 4. The device of clause 3, further comprising a pump fitment securing the metered dose pump to the vial.

Clause 5. The device of any of clauses 1-11, further including a check-valve associated between the metered dose pump and the y-junction.

Clause 6. The device of any of clauses 1-11, further including a nose cone in engagement with the housing.

Clause 7. The device of clause 6 further comprising a dose cap covering the nose cone.

Clause 8. The device of any of clauses 1-11, wherein the third branch of the y-junction is at a 45-degree angle from the base of the y-junction.

Clause 9. The device of any of clauses 1-11, wherein the diffuser is annular.

Clause 10. The device of any of clauses 1-11, wherein the diffuser is a porous material.

Clause 11. The device of any of clauses 1-11, wherein the diffuser forms the bottom of the dose chamber.

Clause 12. A device for the intranasal delivery of a compound, the device comprising:
a housing, the housing including a tip, an actuator, and a dose chamber, the tip and the dose chamber in fluid communication within the housing;
a nozzle at a distal portion of the tip, the nozzle providing an outlet for the compound, the nozzle including a plurality of nozzle openings; and
a pump in fluid communication with the dose chamber, the pump to move the compound into the dose chamber upon actuation of the actuator.

Clause 13. The device of any of clauses 12-15, further comprising a propellant canister associated with the housing, the propellant canister having a propellant valve for actuation by the actuator, the propellant canister in fluid communication with the dose chamber.

Clause 14. The device of clauses 12-15, further comprising a vial of compound associated with the pump to move the compound into the dose chamber from the vial.

Clause 15. The device of clauses 12-15, further including a diffuser.

Clause 16. A device for the intranasal delivery of a compound to the olfactory region of the nasal cavity, the device comprising:
a housing, the housing including a tip, an actuator, and a dose chamber, the tip and the dose chamber in fluid communication with the housing;
a nozzle at a distal portion of the tip, the nozzle providing an outlet for the compound, the nozzle including a plurality of nozzle openings;
a pump in fluid communication with the dose chamber, the pump to move the compound into the dose chamber upon actuation of the actuator;
a propellant canister associated with the housing, the propellant canister having a propellant valve for actuation by the actuator, the propellant canister in fluid communication with the dose chamber; and
a vial of compound associated with the pump to move the compound into the dose chamber from the vial wherein the actuator upon actuation of the device compresses the pump moving the compound into the dose chamber and actuation of the propellant valve disperses the propellant pushing the compound providing for the compound to exit the device through the plurality of nozzle openings.

Clause 17. A kit including the device any of clauses 1-16, a propellant canister and a vial.

The present invention is not to be limited in scope by the specific implementations described herein. Indeed, various modifications of the invention in addition to those described herein will become apparent to those skilled in the art from the foregoing description and accompanying figures. Such modifications are intended to fall within the scope of the appended claims.

The invention claimed is:

1. A device for the intranasal delivery of a compound comprising:
   a y-junction including a base, a first branch of the y-junction radiating from the base, a second branch of the y-junction radiating from the base, and a third branch of the y-junction radiating from the base;
   a vial containing the compound, the vial in fluid communication with the first branch of the y-junction;
   a metered dose pump to move the compound from the vial upon an actuation of the device;
   a dose chamber in fluid communication with the third branch of the y-junction, the dose chamber extending longitudinally from the third branch of the y-junction toward a nozzle, and the dose chamber to receive the compound pumped from the vial;
   the nozzle coupled with the dose chamber to provide an outlet from the dose chamber;
   a propellant canister in fluid communication with the second branch of the y-junction, the propellant canister containing a propellant in liquefied form;
   a diffuser configured to diffuse the propellant from the propellant canister following the actuation of the device; and
   an actuator coupled to the metered dose pump and to the propellant canister, the actuator configured to first actuate the metered dose pump to control movement of the compound from the vial into the dose chamber upon the actuation of the device, and the actuator further configured to subsequently control release of the propellant from the propellant canister, through the diffuser and into the dose chamber after a majority of the compound enters the dose chamber such that propellant pushes the compound as the compound exits the nozzle from the dose chamber.

2. The device of claim 1, further comprising a pump fitment securing the metered dose pump to the vial.

3. The device of claim 1, further including a check-valve coupled to the metered dose pump.

4. The device of claim 1, further including a nose cone in engagement with the nozzle.

5. The device of claim 1, wherein the diffuser is annular.

6. The device of claim 1, wherein the diffuser is a porous material.

7. The device of claim 1, wherein the diffuser forms the bottom of the dose chamber.

8. The device of claim 1, further comprising:
   an internal dose loading channel in a first path for the compound from the vial to the dose chamber,
   wherein the diffuser surrounds the internal dose loading channel in a second path for the propellant from the propellant canister to the dose chamber.

9. The device of claim 1, wherein an angle between the second branch of the y-junction and the third branch of the y-junction is an acute angle.

10. A device for the intranasal delivery of a compound to the olfactory region of the nasal cavity, the device comprising:

a y-junction including a base, a first branch of the y-junction radiating from the base, a second branch of the y-junction radiating from the base, and a third branch of the y-junction radiating from the base;

a vial containing the compound, the vial in fluid communication with the first branch of the y-junction;

a metered dose pump to move the compound from the vial upon actuation of the device;

a dose chamber in fluid communication with the third branch of the y-junction, the dose chamber extending longitudinally from the third branch of the y-junction toward a nozzle, and the dose chamber to receive the compound pumped from the vial;

the nozzle coupled with the dose chamber to provide an outlet from the dose chamber;

a propellant canister in fluid communication with the second branch of the y-junction, the propellant canister containing a propellant in a liquefied form;

a diffuser configured to diffuse the propellant from the propellant canister following the actuation of the device; and an actuator coupled to the metered dose pump and to the propellant canister, the actuator configured to first actuate the metered dose pump to control movement of the compound from the vial into the dose chamber upon the actuation of the device, and the actuator further configured to subsequently control release of the propellant from the propellant canister and into the dose chamber after a majority of the compound enters the dose chamber such that the propellant pushes the compound as the compound exits the nozzle from the dose chamber.

11. The device of claim 10, wherein the propellant canister has a propellant valve for actuation by the actuator, the propellant canister in fluid communication with the dose chamber.

12. The device of claim 10, further comprising:

an internal dose loading channel in a first path for the compound from the vial to the dose chamber, wherein the diffuser surrounds the internal dose loading channel in a second path for the propellant from the propellant canister to the dose chamber.

\* \* \* \* \*